(12) United States Patent
Nakamura (10) Patent No.: US 8,900,208 B2
(45) Date of Patent: *Dec. 2, 2014

(54) GAS MIST PRESSURE BATH SYSTEM

(75) Inventor: Shoichi Nakamura, Higashichikuma-gun (JP)

(73) Assignees: ACP Japan Co., Ltd., Tokyo (JP); Shoichi Nakamura, Higashichikuma-Gun, Nagano (JP)

( * ) Notice: Subject to any disclaimer, the term of this patent is extended or adjusted under 35 U.S.C. 154(b) by 356 days.

This patent is subject to a terminal disclaimer.

(21) Appl. No.: 12/736,735

(22) PCT Filed: Jan. 21, 2010

(86) PCT No.: PCT/JP2010/050666
§ 371 (c)(1),
(2), (4) Date: Nov. 4, 2010

(87) PCT Pub. No.: WO2010/084895
PCT Pub. Date: Jul. 29, 2010

(65) Prior Publication Data
US 2011/0060259 A1   Mar. 10, 2011

(30) Foreign Application Priority Data

Jan. 22, 2009  (JP) .................. 2009-012126
Jan. 22, 2009  (JP) .................. 2009-012127

(51) Int. Cl.
*A61M 35/00*   (2006.01)
*A61H 35/00*   (2006.01)
(Continued)

(52) U.S. Cl.
CPC .............. *A61H 35/00* (2013.01); *A61H 9/0078* (2013.01); *A61K 33/00* (2013.01); *A61K 45/06*
(Continued)

(58) Field of Classification Search
CPC .................. A61H 2201/165; A61H 2205/065; A61H 33/14; A61H 2033/145; A61H 2205/06; A61H 2205/10; A61H 2205/12; A61H 2205/08; A61M 15/0085; A61M 11/005; A61M 15/00; A61M 16/00; A61M 16/16

USPC ................................. 604/289, 290, 303, 305
See application file for complete search history.

(56) References Cited

U.S. PATENT DOCUMENTS

2004/0243026 A1* 12/2004 Toepfer et al. .................. 601/15
2004/0244792 A1* 12/2004 Hashiba .................... 128/200.21
2010/0286750 A1* 11/2010 Nakamura ...................... 607/84

FOREIGN PATENT DOCUMENTS

JP   S61-217132   9/1986
JP   H07-171189   7/1995
(Continued)

*Primary Examiner* — Tatyana Zalukaeva
*Assistant Examiner* — Andrew J Mensh
(74) *Attorney, Agent, or Firm* — Manabu Kanesaka (57) ABSTRACT

The invention is to provide a gas mist pressure bath system, which is possible to control the amount of gas and liquid, pressure and others, and cause a gas mist to be absorbed through a skin and mucous membrane of a human living body under an optimum condition. In the system, a mist is prepared at a density of not less than a predetermined value by pulverizing and dissolving carbon dioxide or oxygen or a mixed gas of carbon dioxide and oxygen and a liquid, and the thus prepared gas mist is directly contacted to the skin and mucous membrane of the living body, and the system comprises a gas supply means 11, a liquid supply means 21, a gas mist supply means 31 for generating and supplying the gas mist generated by storing a liquid inside thereof, and while applying supersonic vibration to the liquid, concurrently injecting a gas into the stored liquid, and a living-body cover member 41 for covering the skin and mucous membrane of the human living body and forming a space for sealing inside the gas mist supplied from the gas mist supply means, and the gas mist within the living-body cover member 41 is caused to contact the skin and mucous membrane of the living body at pressure of not less than a predetermined value.

20 Claims, 10 Drawing Sheets

(51) Int. Cl.
- *A61H 9/00* (2006.01)
- *A61K 33/00* (2006.01)
- *A61K 45/06* (2006.01)
- *A61H 33/04* (2006.01)
- *A61F 13/00* (2006.01)
- *A61H 33/14* (2006.01)
- *A61M 15/00* (2006.01)
- *A61M 11/00* (2006.01)
- *A61M 16/00* (2006.01)
- *A61M 16/16* (2006.01)

(52) U.S. Cl.
CPC .. (2013.01); *A61H 2205/065* (2013.01); *A61H 2205/06* (2013.01); *A61H 33/14* (2013.01); *A61H 2205/10* (2013.01); *A61H 2205/12* (2013.01); *A61H 2205/08* (2013.01); *A61M 15/0085* (2013.01); *A61M 11/005* (2013.01); *A61M 15/00* (2013.01); *A61M 16/00* (2013.01); *A61M 16/16* (2013.01); *A61H 2033/048* (2013.01); *A61H 2033/145* (2013.01); *A61H 2201/165* (2013.01); *A61H 2201/5071* (2013.01); *A61H 2201/5082* (2013.01)

USPC ............ 604/290; 604/289; 604/303; 604/305

(56) References Cited

FOREIGN PATENT DOCUMENTS

| | | | |
|---|---|---|---|
| JP | 2005-058745 | | 3/2005 |
| JP | 2005-205163 | | 8/2005 |
| JP | 2006-026022 | | 2/2006 |
| JP | 2007-014482 | | 1/2007 |
| JP | 2008-168230 | * | 6/2008 |
| JP | U 3144717 | | 8/2008 |
| JP | U 3144718 | | 8/2008 |
| JP | 2009018136 A | * | 1/2009 |
| JP | U 3150690 | | 4/2009 |
| JP | U 3150692 | | 4/2009 |

* cited by examiner

GAS MIST PRESSURE BATH SYSTEM

RELATED APPLICATIONS

The present application is National Phase of International Application No. PCT/JP2010/050666 filed Jan. 21, 2010, and claims priorities from, Japanese Applications No. 2009-012126 filed Jan. 22, 2009 and No. 2009-012127 filed Jan. 22, 2009, the disclosure of which are hereby incorporated by reference herein in its entirety.

TECHNICAL FIELD

The present invention relates to a gas mist pressure bath system, in which a mist (called as "gas mist" hereafter) is prepared by pulverizing and dissolving carbon dioxide or oxygen, or a mixed gas (called as "gas" hereafter) of carbon dioxide and oxygen, and liquid, and the thus prepared gas mist is directly contacted to a skin and mucous membrane of a human living body at pressure of not less than a predetermined value, thereby to improve a gas absorption efficiency into skin and mucous membrane.

BACKGROUND ART

It has conventionally been known that carbon dioxide (carbonic acid anhydride: $CO_2$, called as "carbon dioxide" hereafter) has both properties of being not only soluble in water (water-soluble) but also soluble in fat (fat-soluble) and, therefore, by only contacting the skin and mucous membrane of the living body which is like mixed with water and fat, carbon dioxide penetrates under a subcutaneous layer and expands blood vessels around parts of penetrated carbon dioxide, and it works to improve a blood circulation. Owing to this action of accelerating the blood circulation, it displays various physiological effects such as dropping of blood pressure, improving of metabolism or accelerating to remove pain substance or waste product. Further, it has also anti-inflammation and anti-bacterial. Therefore, carbon dioxide has recently been given attentions also from viewpoints of improving health or beauty other than the purpose of medical cares.

Carbon dioxide in the tissue of the living body works to release oxygen carried in combination with hemoglobin in a red blood cell. Around parts at a high density of carbon dioxide, the red blood cell releases more oxygen. Thus, supply of oxygen to cells by the red blood cell is mainly controlled by carbon dioxide. In short, being without carbon dioxide, hemoglobin remains as combined with oxygen and the cell becomes unable to receive oxygen. As is seen, carbon dioxide seems to be a waste product resulted from action of the cell, however, it plays in fact very important roles in the human living body.

Further, in recent times, oxygen of high density has also widely been known as effective in activity of metabolism, accelerating the blood circulation, fatigue recovery, or stability of blood pressure. Other than them, oxygen has disinfection or sterilization by oxidative effect.

As a prior art for causing carbon dioxide to be absorbed into the living body, a most broadly used technique is (1) a bathing agent issuing carbon dioxide in water. Throwing this bathing agent into hot water in a bathtub, it generates carbon dioxide by reacting carbonate and acid contained in the bathing agent, and dissolves it in hot water. Carbon dioxide dissolved in hot water contacts the skin of a bathing person and penetrates his subcutaneous layer to display physiological effects as above mentioned.

As a prior art for causing more carbon dioxide to contact the living body, (2) a carbon dioxide bathing device is known. This emits and disperses carbon dioxide in hot water and dissolves it at high density. When bathing in hot water dissolving carbon dioxide, the skin directly contacts it like the above mentioned bathing agent.

A blood circulation accelerating device (for example, Patent Document 1) has now been disclosed, which (3) attaches a cover to a human living body on its one part of the surface to form a sealed space together with the human living body, and introduces carbon dioxide into the sealed space from a carbon dioxide supply means for carrying out a carbon dioxide bath.

An inventor of the present invention has proposed a carbon dioxide pressure bath device which is equipped with at least (4) the carbon dioxide supply means, a pressurizing means, and a covering material for covering the skin of the living body and causing carbon dioxide to contact the skin of the living body at pressure of not less than predetermined value.

As a prior art for causing oxygen to be absorbed into the living body, (5) a high density oxygen bathing device has been known. Being similar to the carbon dioxide bathing device, this emits and disperses carbon dioxide in hot water, in which taking a bath, oxygen is caused to directly contact the skin.

CITATION LIST

Patent Documents

Patent Document 1: Japanese Patent Application Publication

SUMMARY OF INVENTION

Problems to be Solved by the Invention

However, each of the above prior arts (1), (2) and (5) dissolves carbon dioxide or oxygen in hot water when taking the bath, and causes carbon dioxide or oxygen to be absorbed into the skin of the living body. Accordingly, they were involved with difficult points of using only when taking the bath. In addition, since carbon dioxide is easily dissolved in water, and even if much consuming it for dissolving in hot water, an absorption rate into the skin is never much high.

On the other hand, since the above prior arts (3) and (4) cause carbon dioxide to directly contact the living body and if comparing with the prior arts (1) and (2), effects are high and efficiency is good. But these have not optimized to control the amount or pressure of carbon dioxide, oxygen and the mist to be introduced into the shielding member (cover).

In view of the above mentioned problems, it is an object of the invention to provide a gas mist pressure bath system which is possible to control the amount, pressure and others of the gas and liquid, and cause the gas mist to be absorbed through the skin and mucous membrane of the human living body under an optimum condition.

Means for Solving the Problems

For solving the above mentioned problems, the present invention is to provide a gas mist pressure bath system, in which a mist (called as "gas mist" hereafter) is prepared at a density of not less than a predetermined value by pulverizing and dissolving carbon dioxide or oxygen, or a mixed gas (called as "gas" hereafter) of carbon dioxide and oxygen and a liquid, and the thus prepared gas mist is directly contacted to a skin and mucous membrane of a living body. The system comprises a gas supply means, a liquid supply means, a gas mist supply means for generating and supplying the gas mist by storing the liquid inside thereof, and while injecting a gas into the stored liquid, concurrently applying supersonic vibration to this liquid, and a living-body cover member for covering the skin and mucous membrane of the living body and forming a space of sealing inside the gas mist supplied from the gas mist supply means, and the present gas mist pressure bath system is characterized by causing the gas mist within the living-body cover member to contact the skin and mucous membrane of the living body at pressure of not less than a predetermined value.

By the way, the invention refers it as "pulverizing and dissolving" to pulverize the liquid into fine liquid drops, and cause to contact and mix with gas (carbon dioxide, or oxygen, or a mixed gas of carbon dioxide and oxygen).

Herein, more desirably, the above mentioned gas mist pressure bath system of the invention is further provided with a sensor for measuring supplying conditions of the gas, liquid and gas mist, and control means for controlling supplies of the gas, liquid and gas mist based on the measuring values of the sensors.

In addition, the above gas mist pressure bath system is desirably further provided with a pressurizing means for pressurizing the living-body cover member.

The control means may supply the gas mist intermittently into the living-body cover member to perform interval pressurization (pulse pressurization) thereon. Otherwise, the pressurizing means may pressurize the living-body cover member intermittently to perform the interval pressurization (pulse pressurization) thereon.

It is optimum that the above mentioned liquid is any one or plural combination of water, ionic water, physiological salt solution, ozone water, purified water or sterilized water. This liquid desirably further contains any one or plural combination of menthol, vitamin E, vitamin C derivative, retinol, anesthetic, cyclodextrin, photocatalyst, complex of photocatalyst and apatite, hyaluronic acid, coenzyme Q10, seed oil, propolith, ethanol, gluconic acid chlorohexizine, amphoteric surface active agent, benzalkonium chloride, alkyldiamino ether glycin acetate, sodium hypochlorite, acetyl hydroperoxide, sodium sesquicarbonate, silica, povidone-iodine, sodium hydrogen carbonate, high density carbonate spring, anti-allergic agent, anti-inflammatory agent, anti-febrile, anti-fungus agent, anti-influenza virus, carcinostatic substance, anti-hypertensive agent, cosmetic agent, or trichogen.

Preferably, the liquid is supplied into the gas mist supply means under a condition of being heated. Grain sizes of the gas mist supplied from the gas mist supply means into the living-body cover member are suitably not more than 10 μm.

The control means preferably holds pressure at 1.02 to 2.5 air pressure in the living-body cover member when taking the gas mist bath.

There may be provided an electric charge supply means for supplying charge to the mist from the gas mist supply means. At this time, the charge is preferably a minus charge.

Desirably, the gas mist supply means has a gas mist supply pipe for supplying the gas mist into the living-body cover member, and this gas mist supply pipe has a filter for removing liquid drops attached to a pipe inside. Further, a whole or one part of the gas mist supply pipe is suitably composed of a cornice shaped pipe, and this gas mist supply pipe is provided with a check valve.

In addition, the gas mist supply portion of the living-body cover member is also provided at its supply portion with the check valve.

Further, the gas mist supply means has a storage for storing the liquid and the gas mist. The storage is shaped in dome of convex having a curved face toward an upper portion and is formed with a gas mist exhaust portion at the dome shaped top. The gas mist supply means has desirably one or plurality of pored plates for refining the gas mist in the storage.

The control means stops the gas from the gas supply means when the pressurizing value within the living-body cover member is higher than the predetermined value.

Advantageous Effect of the Invention

According to the gas mist pressure bath system of the invention, since it is possible to control the amount and pressure of the gas mist in the living-body pressure bath cover by the control device, the gas mist bath can be always taken under the best condition.

Further, pressurization into the living-body pressure bath cover is easy, and a skin-pass breath of the gas can be carried out more efficiently.

DESCRIPTION OF EMBODIMENTS

In the following description, explanations will be made to embodiments of this invention, referring to the attached drawings.

First Embodiment

Figure 1:
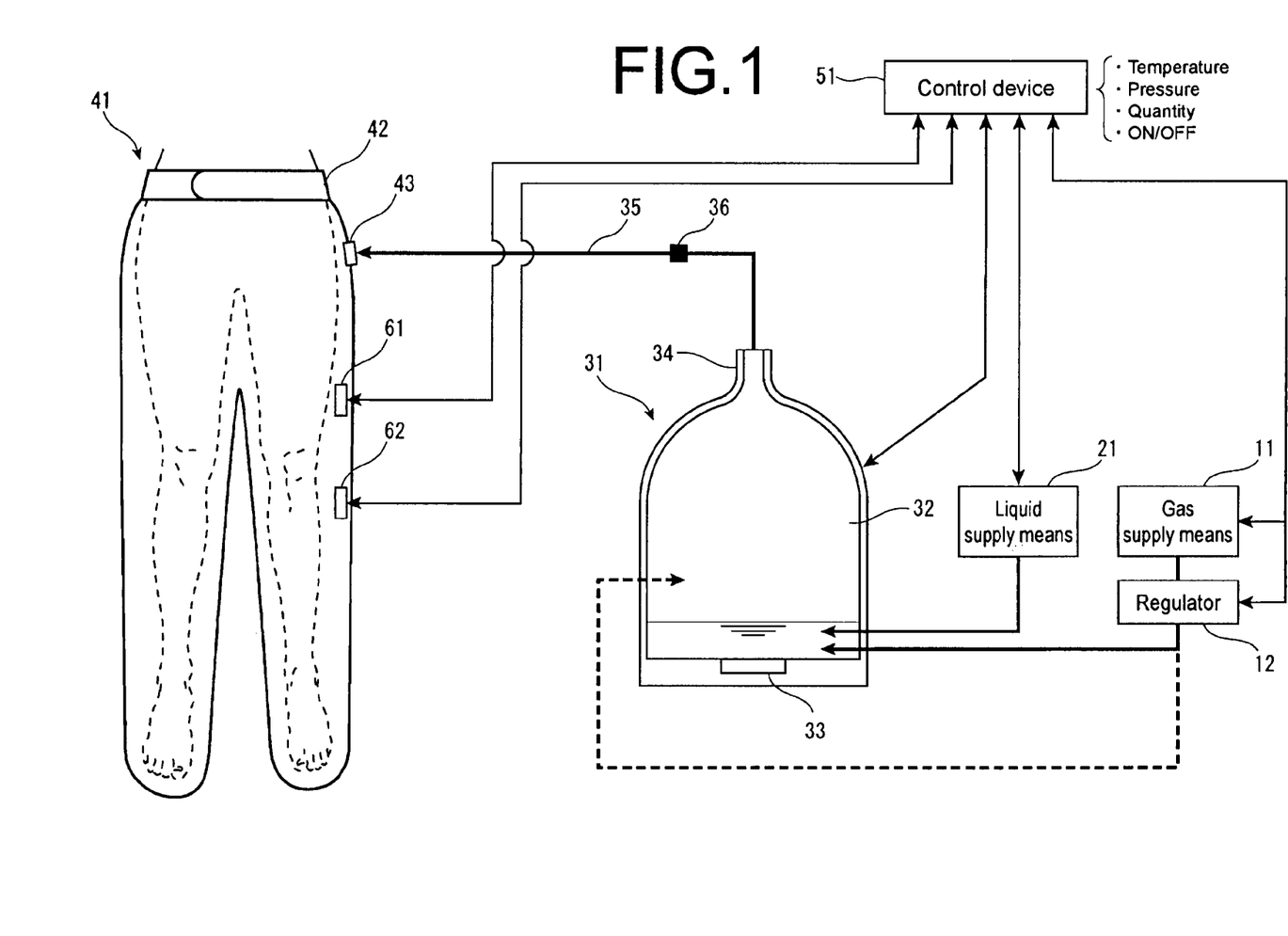
FIG. 1 A generally schematic view of the gas mist pressure bath system depending on a first embodiment of the invention.

FIG. 1 is the generally schematic view of the gas mist pressure bath system depending on the first embodiment of the invention. As shown in this view, the gas mist pressure bath system of this embodiment comprises the gas supply means 11, the liquid supply means 21, the gas mist supply device 31 of storing the liquid inside and while injecting the gas into the stored liquid, concurrently applying supersonic vibration to this liquid, thereby to generate the mist (called as "gas mist" hereafter) by pulverizing and dissolving the gas and the liquid, and supplying it under pressurization, the living-body pressure bath cover 41 of forming a space for sealing the supplied gas mist, and the control device 51 for generating and controlling to supply the gas mist.

The gas supply means 11 supplies the gas into the liquid stored in the gas mist supply device 31, provided that if the gas mist is enough supplied in the living-body pressure bath cover 41, the gas is not supplied into the stored liquid, but directly supplied into the storing part 32 of the gas mist supply device 31 as shown with a dotted line in FIG. 1. As the gas supply means 11, to use a gas bomb is optimum. The gas supply means 11 is provided with a regulator 12 for adjusting gas pressure. Omitting illustration, the gas supply means 11 may be disposed with a heater for heating the gas or a thermometer for controlling temperatures.

The liquid supply means 21 is composed of such as a pump and supplies water to the gas mist supply device 31. As the liquid, it is suitable to use water, ionic water, physiological salt solution, ozone water, purified water or sterilized water. Further, these liquids may contain medicines useful to user's diseases or symptoms. For the medicines, enumerated are, for example, anti-allergic agent, anti-inflammatory agent, anti-febrile, anti-fungus agent, anti-influenza virus, carcinostatic substance, anti-hypertensive agent, cosmetic agent, or trichogen. Further, these liquids are further possible to generate synergistic effects by coupling with a gas physiological action with single or plurality of menthol having a cooling action; vitamin E accelerating circulation of the blood; vitamin C derivative easily to be absorbed to a skin tissue and having a skin beautifying effect; retinol normalizing a skin heratinizing action and protecting the mucous membrane; anesthetic moderating irritation to the mucous membrane; cyclodextrin removing odor; photocatalysis or a complex of photocatalysis and apatite having disinfection and anti-phlogistic; hyaluronic acid having excellent water holding capacity and a skin moisture retention effect; coenzyme Q10 activating cells and heightening immunization; a seed oil containing anti-oxidation and much nutrient; or propolith having anti-oxidation, anti-fungus, anti-inflammatory agent, pain-killing, anesthetic, and immunity. Otherwise, the liquids may be added with ethanol, gluconic acid chlorohexizine, amphoteric surface active agent, benzalkonium chloride, alkyldiamino ether glycin acetate, sodium hypochlorite, acetyl hydroperoxide, sodium sesquicarbonate, silica, povidone-iodine, sodium hydrogen carbonate. In addition, high density carbonate spring may be added (as examples organic components, sulfate, carbonate, sodium dichloroisocyanurate) having main components of carbonate and organic acid.

By the way, in the liquid supply means 21, it is desirable to dispose a heater (not shown) heating the liquid (for example, heating to a hot water of around 40° C.) or a thermometer (not shown) controlling temperature.

The gas mist supply device 31 has the storage 32 for storing the liquid and the gas mist, a supersonic vibrator 33 of applying supersonic vibration to the liquid stored in the storage 32 and a gas mist exhaust portion 34 of exhausting the generated gas mist. Although omitting illustration, there are provided respectively a gas supply portion and a liquid supply portion for guiding gas from the gas supply means 11 and liquid from a liquid supply means 21 to the storage 32.

The gas is discharged from the gas supply means 11 into the liquid stored in the storage 32. By discharging the gas into the liquid, the gas can be dissolved in the liquid. Supersonic vibration is added by the supersonic vibrator 33 to the liquid having dissolved the gas. The supersonic vibrator 33 has a piezoelectric element, which is so disposed that its plane of vibration is exposed to the storage 32 and directly contacts the liquid, or contacts the bottom of the storage 32. When operating the piezoelectric element, supersonic vibration is transmitted to the liquid, and at the same time fine liquid drops occur from the liquid surface, and are pulverized and dissolved together with the supplied gas and turn out the mist. Grain sizes of the mist generated at this time are desirably fine, and being less than 10 μm is optimum.

The generated gas mist spreads over inside of the storage 32 and is discharged from the gas mist exhaust portion 34 following a gas convection. Herein, it is desirable that the storage 32 is shaped in convex doom toward an upper portion having a curved face as shown in FIG. 1. The gas mist exhaust portion 34 is provided at a head top of the doom shape. By shaping such a form, it is possible that the gas mist is more stored, while preventing that the mist contacts the top portion of the inside wall of the storage 32 and reverts to the liquid.

The gas mist discharged from the gas mist exhaust portion 34 is supplied into the living-body pressure bath cover 41 via the gas mist supply pipe 35. The gas mist supply pipe 35 is connected to a supply portion 43 of the living-body pressure bath cover 41, and is desirably furnished with a liquid drop removing filter 36 for removing excessive liquid drop attached to the pipe inside. Although not illustrating, the gas mist supply pipe 35 is provided inside with a check valve for checking back-flow of the gas mist and the gas.

Figure 2:
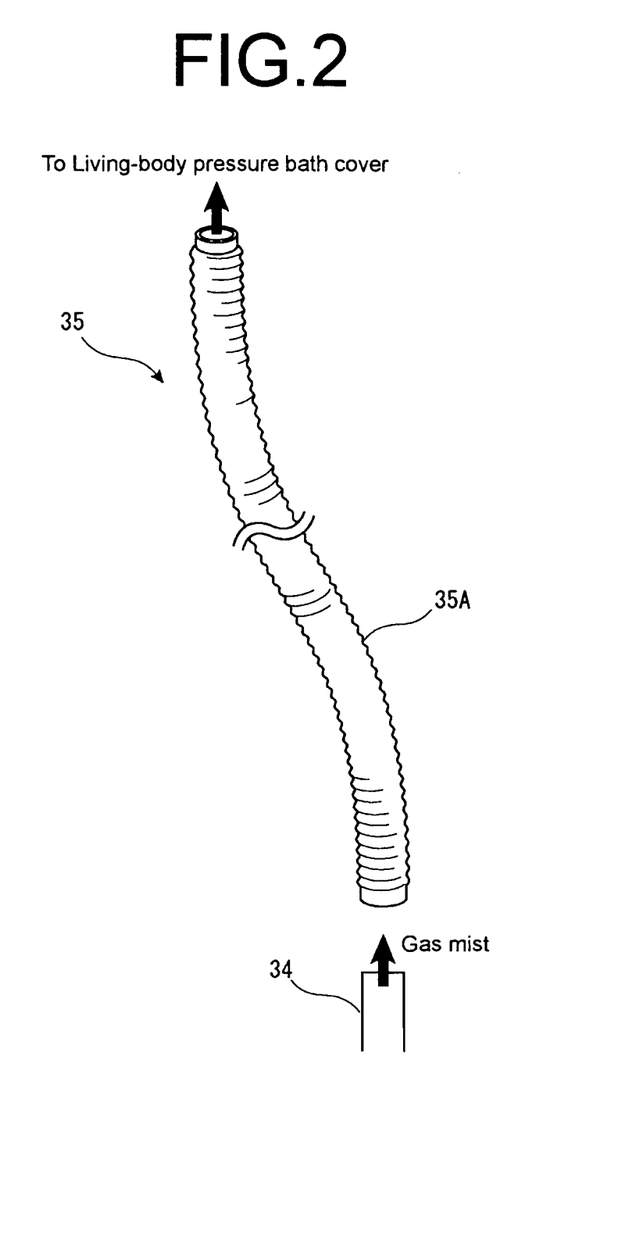
FIG. 2 A typical view showing one example of the gas mist supply pipe used to the gas mist pressure bath system depending on the invention.

Further, as shown in FIG. 2, preferably, the gas mist supply pipe 35 is overall or partially composed of a soft cornice shaped pipe 35A of a large diameter. If composing with such a corniced pipe 35A, the gas mist supply pipe 35 is freely bent and may be expanded so that the system user is not restricted in action. Even if the gas mist flowing in the gas mist supply pipe 35 becomes gradually liquefied, the liquid can be removed through concaves and convexes of the cornice.

Figure 3:
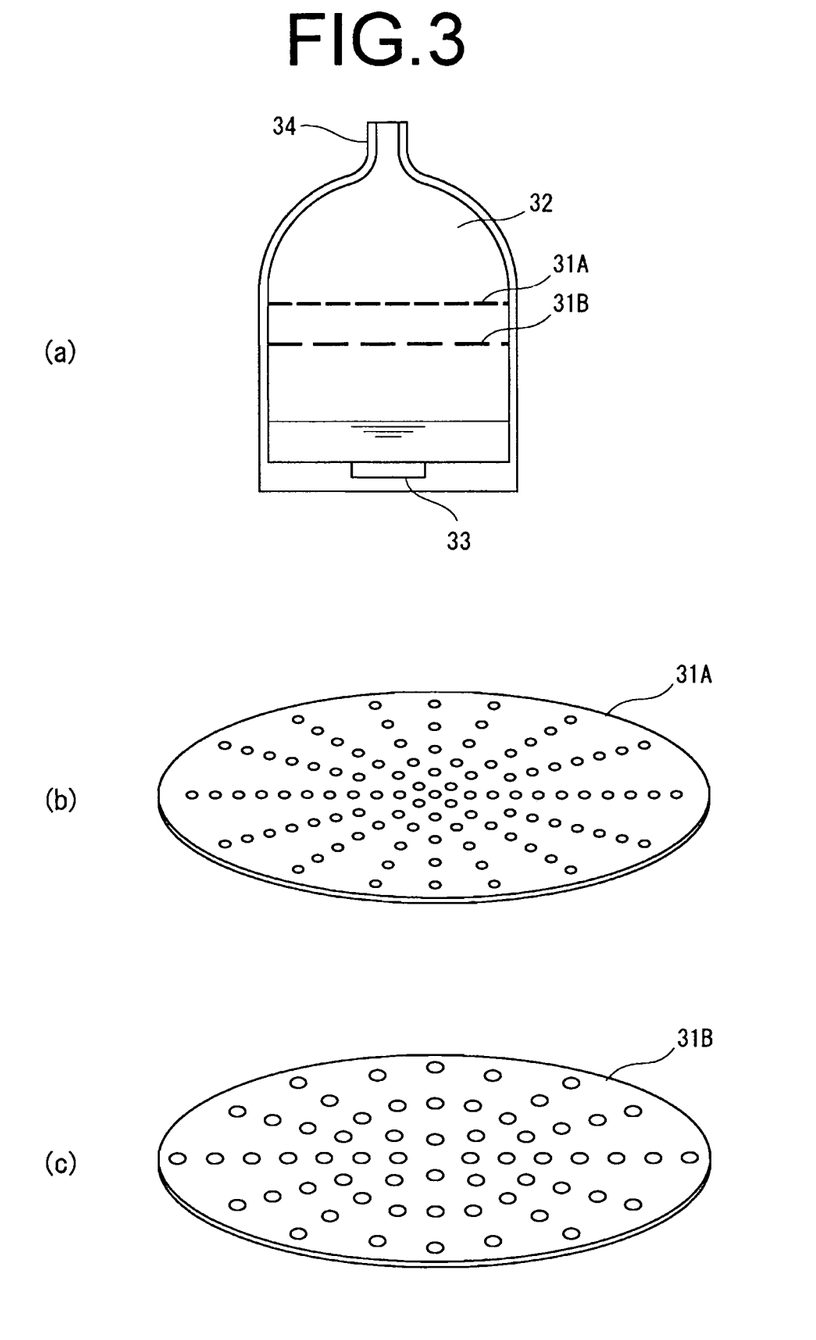
FIG. 3 Typical views showing examples of plates arranged in the gas mist supply device of the gas mist pressure bath system depending on the invention.

The gas mist supply device 31 may be, as shown in FIG. 3(a), furnished inside with one or plural sheets of plates 31A, 31B (in FIG. 3, as the example, two sheets). The plates 31A, 31B are, as shown in FIG. 3(b), (c), formed with plural pores, and the generated gas mist is further refined when passing through the pores. Then, with respect to the upper plate 31A and the lower plate 31B, it is preferable that the diameter of the upper plate 31A is smaller than that of the lower plate 31B.

The living-body pressure bath cover 41 may form a space for covering the skin and mucous membrane of the living body (herein, as the example, a lower extremity) and sealing the gas mist and the gas inside. The living-body pressure bath cover 41 is composed of a pressure resistant, non-air permeable and non-moisture permeable material, for example, preferably, the natural rubber, silicone rubber, polyethylene, polypropylene, polyvinylidene, polystylene, polyvinylacetate, polyvinyl chloride, polyamide resin, polytetrafluoroethylene. The living-body pressure bath cover 41 has a supply portion 43 for introducing the gas mist and the gas inside. The supply port 43 is inside provided with a check valve for checking back flow of the gas mist and the gas. The living-body pressure bath cover 41 may be provided with an opening or a valve for exhausting the gas and the gas mist. The pressure control may be carried out manually, but as later mentioned, desirably automatically by a control device 51 together with supply control of the gas and the gas mist on the basis of measuring values of the manometer 61. A safety valve (recess valve) may be provided for automatically opening a valve when the inside of the living-body pressure bath cover 41 becomes more than a constant pressure.

The living-body pressure bath cover 41 is inside installed with a manometer 61 for measuring an inside pressure. The control device 51 controls supply of the gas mist and the gas on the basis of measuring values of the manometer 61 for maintaining a pressure value within the living-body pressure bath cover 41 to be more than 1 air pressure (more preferably, around 1.02 to 2.5 air pressure). For example, the control device 51 controls or stops the supply of the gas or the gas mist from the gas mist supply device 31, or exhausts the gas or the gas mist from the living-body pressure bath cover 41. Further, the living-body pressure bath cover 41 is inside installed with a thermometer 62 for measuring an inside temperature within the living-body pressure bath cover 41. The control device 51 performs on-off of a heater installed in the liquid supply means 21 on the basis of measuring values of a manometer 62 for maintaining a predetermined temperature (for example, around 38° C.) bringing about warm bath effects within the living-body pressure bath cover 41.

The living-body pressure bath cover 41 has, around its opening, a stopper 42 for attaching to and detaching from the living body (herein, as the example, the lower extremity) and stopping leakage of the gas mist and the gas. The stopper 42 is suitably composed of, e.g., a stretching face fastener, or may have a sole string or rubber or their combination. For heightening a sealing property in the living-body pressure bath cover 41, the inside (that of the stopper 42) may have a material attaching to the user's skin. The adhesive material is preferably a visco-elastic gel of polyurethane or silicone rubber. Further, this adhesive material is detachably used and exchangeable each time or if viscosity becomes weak.

The control device 51 is composed of a computer having CPU, memory and display. This performs various kinds of controls such as pressure control or on-off switch of the gas from the gas supply means 11; supply pressure or temperature of the liquid from the liquid supply means 21; on-off switch of supply; on-off switch of the supersonic vibrator 33 of the gas mist supply device 31; on-off switch of the gas mist in order to perform the gas mist pressure bath under an optimum condition. In particular, it is preferable to compose a structure when the pressure value becomes a predetermined value in the living-body pressure bath cover 41, supplying of the gas from the gas supply means 11 is stopped by the control device 51.

For carrying out the gas mist pressure bath by using the gas mist pressure bath system of the present embodiment, the living-body pressure bath cover 41 is secured to the living body (herein, as the example, the lower extremity) and closed. The liquid is supplied from the liquid supply means 21 to the gas mist supply device 31, and the gas is supplied from the gas supply means 11 into this liquid. Subsequently, by turning on the supersonic vibrator 33, the gas mist is generated by the supersonic wave. Then, the control device 51 controls the supplying pressure, amount, temperature and others of the liquid and the gas. The generated gas mist is supplied from the supply portion 43 into the living-body pressure bath cover 41. When the mist is enough filled in the living-body pressure bath cover 41, the gas is directly supplied from the gas supply means 11 into the storage 32 of the gas mist supply device 31, not into the stored liquid. When the inside of the living-body pressure bath cover 41 becomes an optimum pressurized and heated condition (around 1.02 to 2.5 air pressure and around 38° C.) in view of the measuring values of the manometer 61 and the thermometer 62, the control device 51 once stops supply of the gas mist or the gas and under this condition the gas mist pressure bath is carried out.

The above mentioned explanation has been made with the example of the lower extremities of the living body, and the invention is applicable to various parts. Then, the optimum gas mist pressure bath is performed using the living-body pressure bath cover 41 meeting object parts of the living body.

Figure 4:
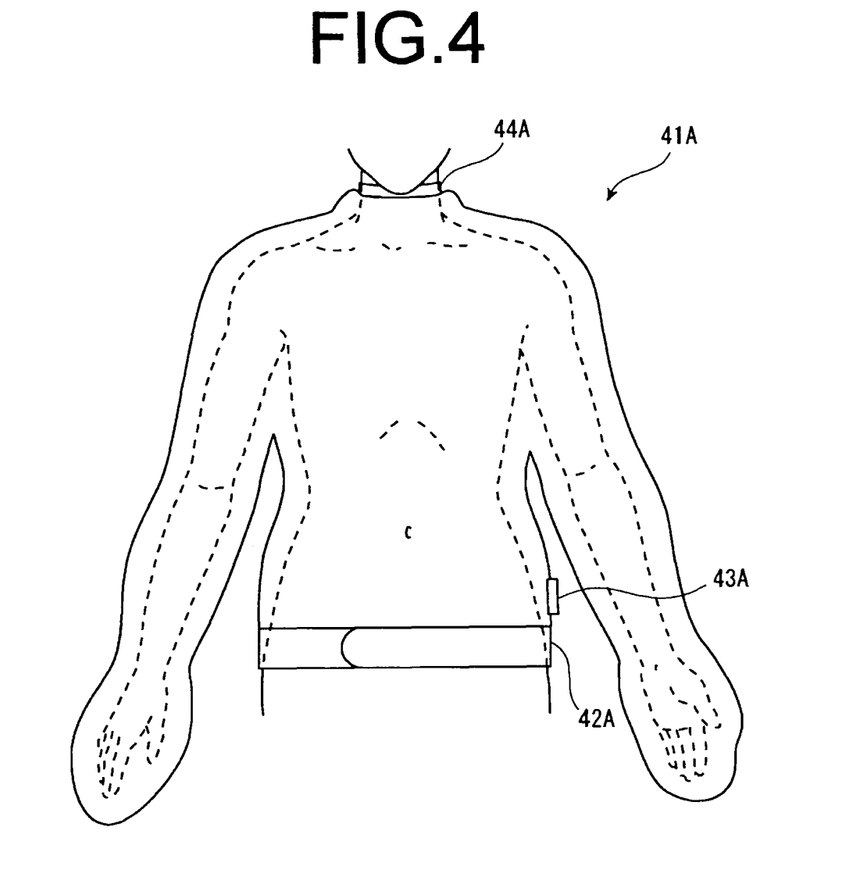
FIG. 4 A typical view showing a configuration example (No. 1) of the living-body pressure bath cover of the gas mist pressure bath system depending on the first embodiment of the invention.
Figure 5:
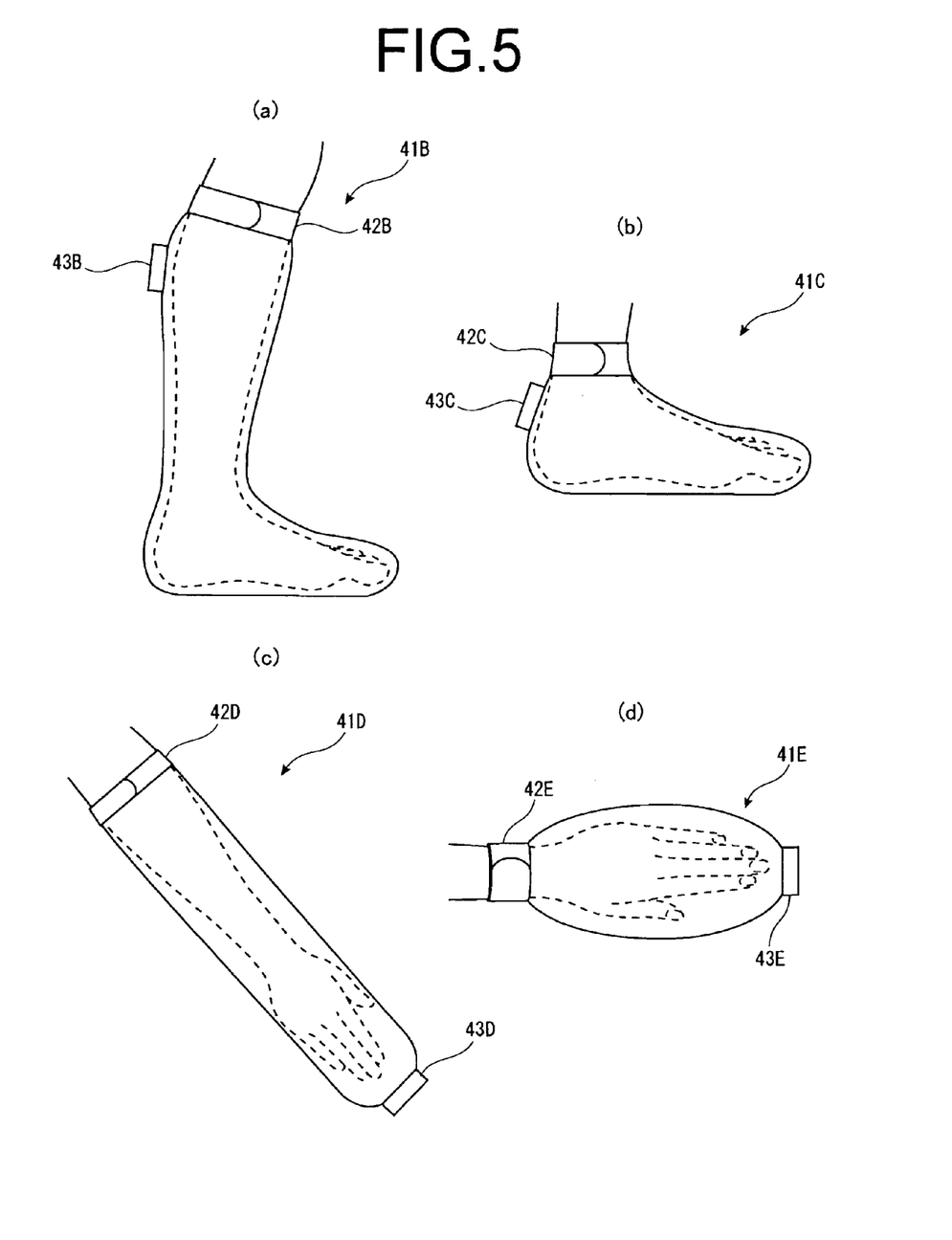
FIG. 5 A typical view showing a configuration example (No. 2) of the living-body pressure bath covers of the gas mist pressure bath system depending on the first embodiment of the invention.
Figure 6:
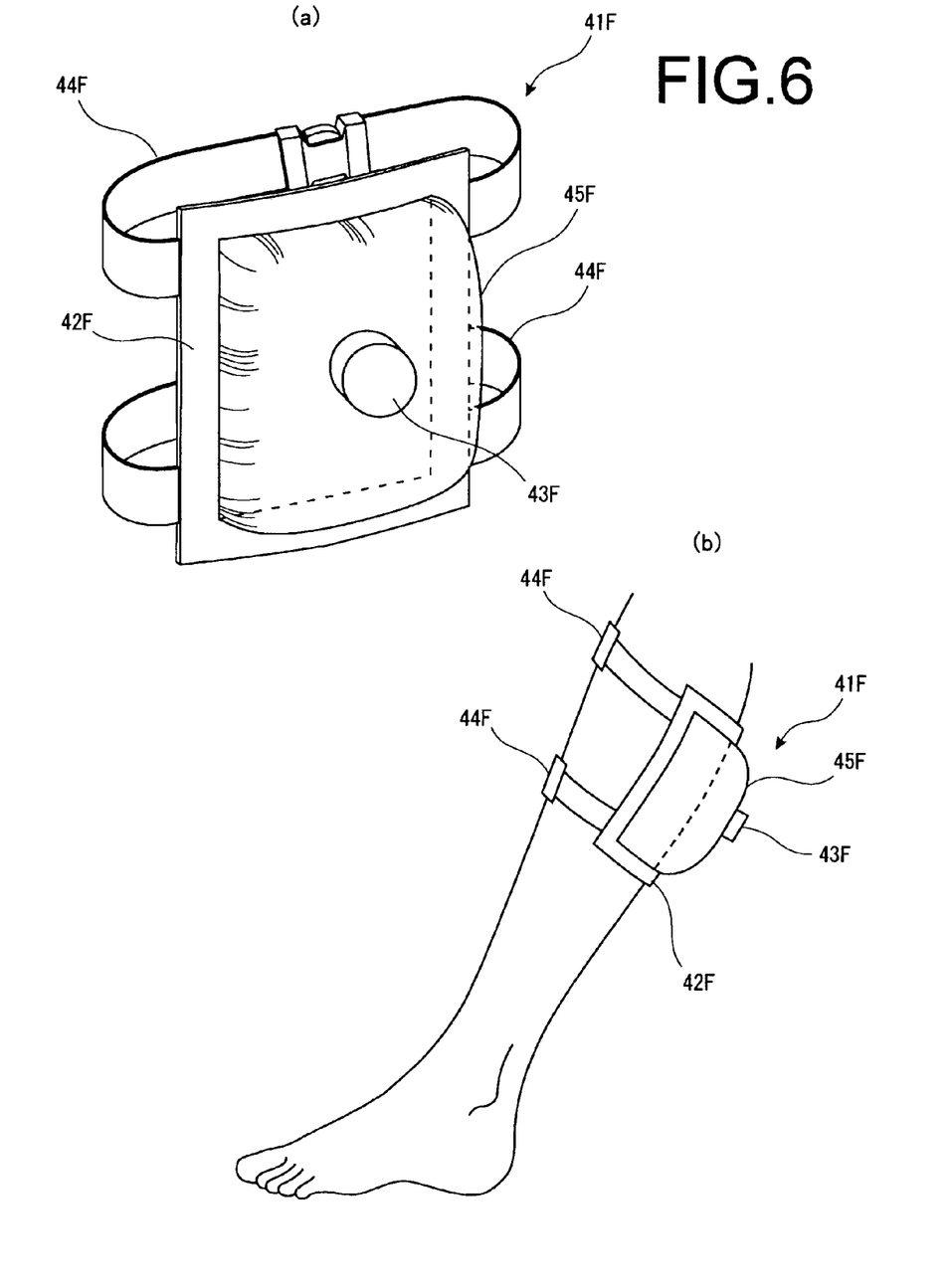
FIG. 6 A typical view showing a configuration example (No. 3) of the living-body pressure bath cover of the gas mist pressure bath system depending on the first embodiment of the invention.

FIGS. 4 to 6 show the various shaped examples of the living-body pressure bath covers 41. At first, FIG. 4 shows the schematic view of the living-body pressure bath cover 41A for the upper half of the body. The living-body pressure bath cover 41A has a shape for wrapping the whole of the upper half of the body, and has a stopper 42A for attaching to and detaching from the living body and stopping leakage of the gas mist and the gas. A similar stopper 44A is formed around the opening of a neck. 43A designates a supply portion for introducing the gas mist and the gas inside.

FIG. 5 shows the various shaped examples of the living-body pressure bath covers 41 for covering further limited parts of the living body. FIG. 5(a) is a living-body pressure bath cover 41B for one-side lower extremity (lower part under a knee) of the living body. The living-body pressure bath cover 41B has a stopper 42B at its opening part and a supply portion 43B for introducing the gas mist and the gas inside. FIG. 5(b) is a living-body pressure bath cover 41C for a foot of the living body. The living-body pressure bath cover 41C has a stopper 42C at its opening part and a supply portion 43C for introducing inside the gas mist and the gas. FIG. 5(c) is a living-body pressure bath cover 41D for an arm of the living body. The living-body pressure bath cover 41D has a stopper 42D and a supply portion 43D for introducing inside the gas mist and the gas. FIG. 5(d) is a living-body pressure bath cover 41E for a hand of the living body. The living-body pressure bath cover 41E has a stopper 42E and a supply portion 43E for introducing inside the gas mist and the gas.

Further, FIG. 6 shows a patch shaped living-body pressure bath cover 41F. FIG. 6(a) is a view showing an outline of the patch shaped living-body pressure bath cover 41F. FIG. 6(b) is a view showing an external appearance when attaching the patch shaped living-body pressure bath cover 41F to the living body (herein, lower extremity of the living body). The living-body pressure bath cover 41F is composed of a cover part 45F for covering the skin and mucous membrane of the living body, a stopper 42F provided at the margin of the cover part 45F and directly attached to the skin and mucous membrane of the living body, a supply portion 43F for supplying the gas mist and the gas into a space defined by the cover part 45F and the stopper 42F, and fasteners 44F made of belts or strings for fastening the cover part 45F to the living body.

In regard to the living-body pressure bath covers 41, other than the examples shown in FIGS. 4 to 6, various shapes may be assumed. In sum, if forming the space for sealing the gas mist and the gas inside, any shape is sufficient. An exhaust portion may be formed for exhausting the gas mist and the gas from the inside of the living-body pressure bath covers 41. In addition, the invention may be applied not only to the human living body but to animals.

In addition, since pressurization in the gas mist pressure bath heightens the effects by pressurizing in pulsing at predetermined interval, the control device 51 may supply the gas mist into the living-body pressure bath cover 41 intermittently at fixed rhythm. As to the pressurizing interval at such a case, if synchronizing with pulsations, the effects are more heightened.

Second Embodiment

Figure 7:
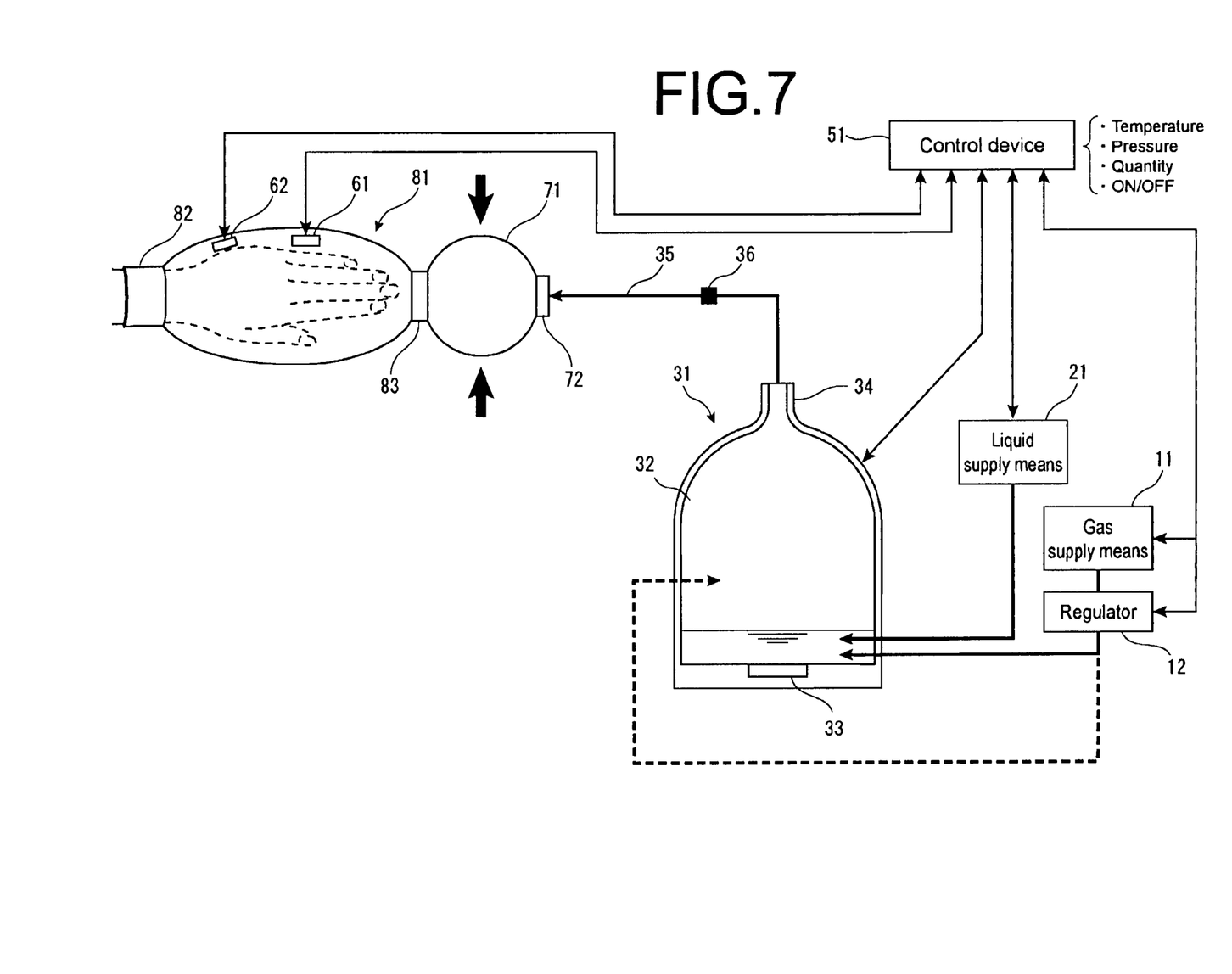
FIG. 7 A generally schematic view of the gas mist pressure bath system depending on a second embodiment of the invention.

FIG. 7 is the whole schematic view of the gas mist pressure bath system depending on the second embodiment of this invention. This embodiment will explain the gas mist pressure bath system further having a pressurizing means for simplifying pressurization within the living-body pressure bath cover. As to the same parts as those of the first embodiment shown in FIG. 1, the same numerals will be given, and detailed explanation will be omitted.

As shown in FIG. 7, the gas mist pressure bath system of this embodiment has a living-body pressure bath cover 81 forming a space into which the gas mist and the gas are sealed and a pressurizing part (gas storage) 71 connecting the living-body pressure bath cover 81 and pressurizing therein.

The living-body pressure bath cover 81 has almost the same structure of the living-body pressure bath cover 41 of the first embodiment, and has a stopper 82 and a gas mist and gas supply portion 83, provided herein that the supply portion 83 is connected to the pressurizing part 71. By the way, the example hereof illustrates the living-body pressure bath cover 81 of a shape for covering a hand of the human living body.

The pressurizing part 71 is the hollow gas storage connecting the living-body pressure bath cover 81 and pressurizing therein. The pressurizing part 71 is connected to the supply portion 83 of the living-body pressure bath cover 81 and has also a supply portion 72 of itself from which the gas mist or the gas are supplied therein. The supply portion 72 of the pressurizing part 71 is also provided with the check valve for checking back flow of the gas mist and the gas. After storing the gas mist or the gas in the pressurizing part 71, if pressurizing as crushing the pressurizing part 71 as showing with arrows, since the gas mist or the gas in the pressurizing part 71 are exhausted as escaping into the living-body pressure bath cover 81, the inside of the living-body pressure bath cover 81 can be pressurized.

The pressurizing part 71 may be structured as pressing manually, and mechanically by controlling the control means 51 using a driving device. As mentioned above, pressurization in the gas mist pressure bath heightens effects by performing an interval pressurization in pulse, and so the pressurizing part 71 may be pressed intermittently. The pressurizing interval heightens effects by synchronizing with pulsation of pulse.

For carrying out the gas mist pressure bath by using the gas mist pressure bath system of the present embodiment, the living-body pressure bath cover 81 is secured to the living body (herein, as the example, the hand of the human living body) and closed. The liquid is supplied from the liquid supply means 21 to the gas mist supply device 31, and then the gas is supplied into this liquid from the gas supply means 11. Subsequently, by turning on the supersonic vibrator 33, the gas mist is generated by the supersonic-wave. Then, the control device 51 controls the supplying pressure, amount, temperature and others of the liquid and the gas. The generated gas mist is supplied from a supply portion 83 into the living-body pressure bath cover 81 via the pressurizing part 71. When the mist is enough filled in the living-body pressure bath cover 81, the gas is directly supplied from the gas supply means 11 into the storage 32 of the gas mist supply device 31, not into the stored liquid. The control device 51 so controls that the inside of the living-body pressure bath cover 81 is to be at an optimum temperature (for example, around 38° C.) from the measuring values of the manometer 62. When the gas mist or the gas of the optimum amount are stored in the living-body pressure bath cover 81 and the pressurizing part 71, the pressurizing part 71 is pressurized as crushed. Thereby, the gas mist or the gas in the pressurizing part 71 are exhausted into the living-body pressure bath cover 81, and the inside of the living-body pressure bath cover 81 is pressurized moderately (around 1.02 to 2.5 air pressure) and the gas mist pressure bath is carried out.

As having mentioned in the first embodiment, since the living-body pressure bath cover 81 is applied to various parts of the living body, many shapes may be used, provided in this embodiment that shapes (size) must be easily pressurized by the pressurizing part 71. This substantially depends on the dimension of the pressurizing part 71. Actually, so far as pressurizing means are any one, the pressurizing part 71 is desirably compact as not demanding large spaces, and accordingly, the living-body pressure bath cover is also desirably applied to comparatively compact objects (covering limited parts of the living body).

Figure 8:
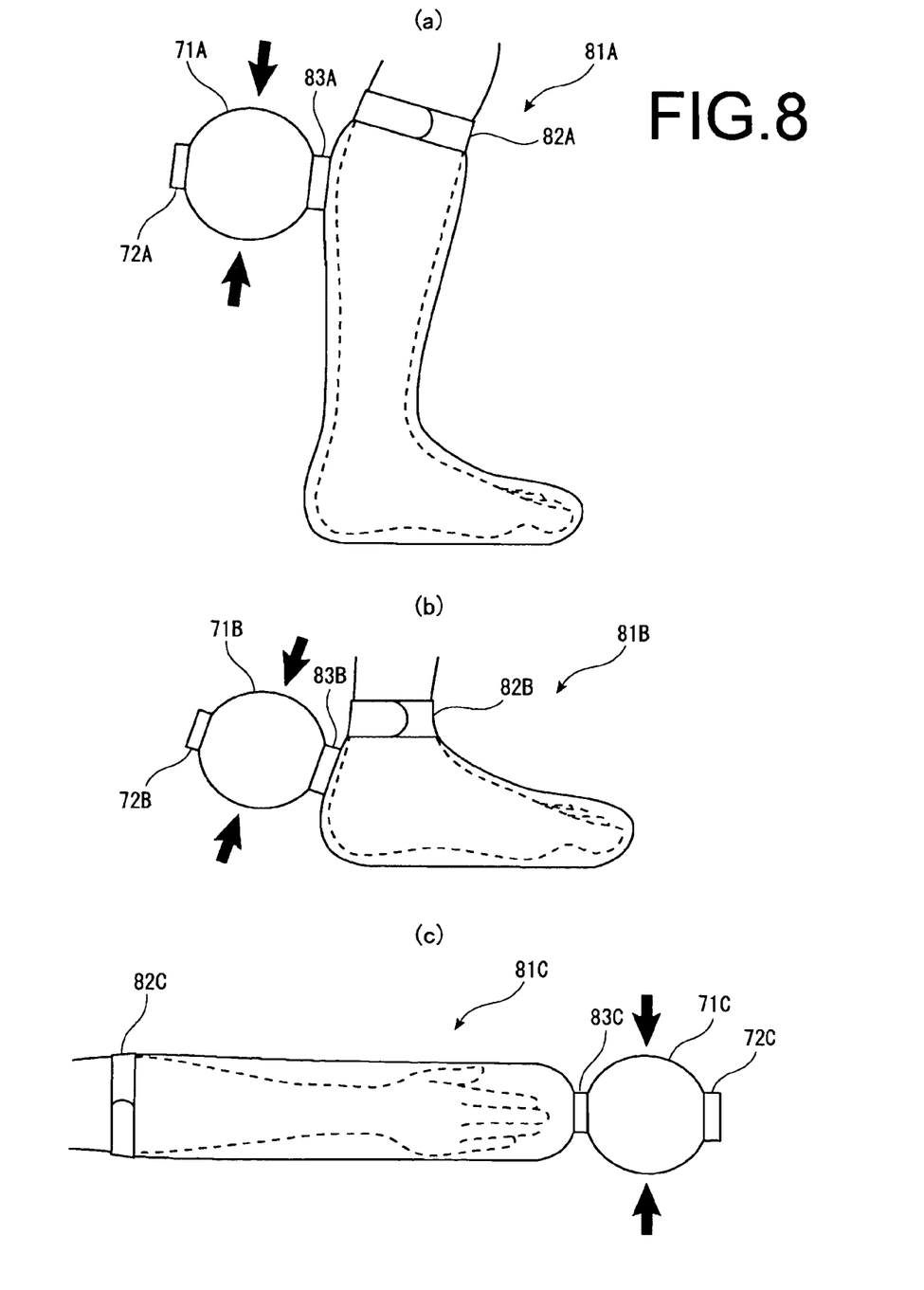
FIG. 8 A typical view showing a configuration example (No. 1) of the living-body pressure bath cover of the gas mist pressure bath system depending on the second embodiment of the invention.
Figure 9:
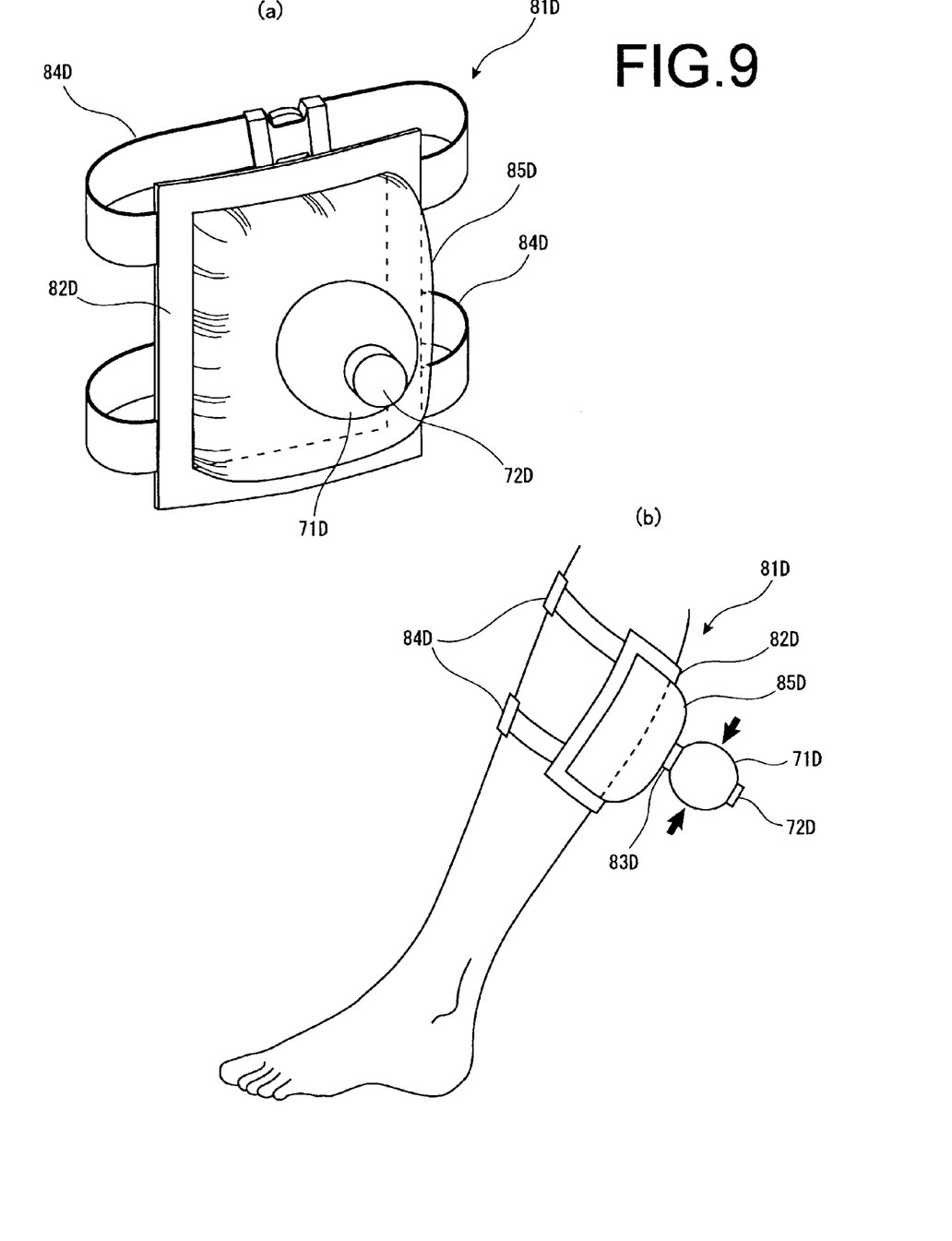
FIG. 9 A typical view showing a configuration example (No. 2) of the living-body pressure bath cover of the gas mist pressure bath system depending on the second embodiment of the invention.

FIGS. 8 and 9 show examples of the living-body pressure bath cover 81 and the pressurizing part 71 connected thereto. FIG. 8(a) is a living-body pressure bath cover 81A for one-side lower extremity (lower part under a knee) of the living body. The living-body pressure bath cover 81A has a stopper 82A at its opening part and a supply portion 83A for introducing inside the gas mist and the gas. The supply portion 83A is connected to the pressurizing part 71A, and the gas mist and the gas are supplied into the living-body pressure bath cover 81A through a supply portion 72A of a pressurizing part 71A. FIG. 8(b) is a living-body pressure bath cover 81B for a foot of the living body. The living-body pressure bath cover 81B has a stopper 82B and a supply portion 83B for introducing the gas mist and the gas into the inside thereof. The supply portion 83B is connected to a pressurizing part 71B, and the gas mist and the gas are supplied into the living-body pressure bath cover 81B through a supply portion 72B of a pressurizing part 71B. FIG. 8(c) is a living-body pressure bath cover 81C for an arm of the living body. The living-body pressure bath cover 81C has a stopper 82C at its opening part and a supply portion 83C for introducing the gas mist and the gas into the inside thereof. The supply portion 83C is connected to a pressurizing part 71C, and the gas mist and the gas are supplied into the living-body pressure bath cover 81C through a supply portion 72C of a pressurizing part 71C.

FIG. 9 shows a patch shaped living-body pressure bath covers 81D. FIG. 9(a) is a view showing an outline of the patch shaped living-body pressure bath covers 81D. FIG. 9(b) is a view showing an external appearance when attaching the patch shaped living-body pressure bath covers 81D to the living body (herein, lower extremity of the living body). The living-body pressure bath covers 81D is composed of a cover part 85D for covering the skin and mucous membrane of the living body, a stopper 82D provided at the margin of the cover part 85D and directly attached to the skin and mucous membrane of the living body, a supply portion 83D for supplying the gas mist and the gas into a space defined by the cover part 85D and the stopper 82D, and fasteners 84D made of belts or strings for fastening the cover part 85D to the living body. The supply portion 83D is connected to a pressurizing part 71D, and through a supply portion 72D of a pressurizing part 71D, the gas mist and the gas are supplied into the living-body pressure bath cover 81D.

An exhaust portion may be formed for exhausting the gas mist and the gas from the inside of the living-body pressure bath cover 81. In addition, the invention may be applied not only to the human living body but to animals.

In the above embodiment, the pressurizing part 71 is the hollow gas storage connected to the living-body pressure bath cover 81, and so far as materials of easily pressurizing as crushing externally the living-body pressure bath cover 81 itself, any materials are sufficient.

Third Embodiment

Figure 10:
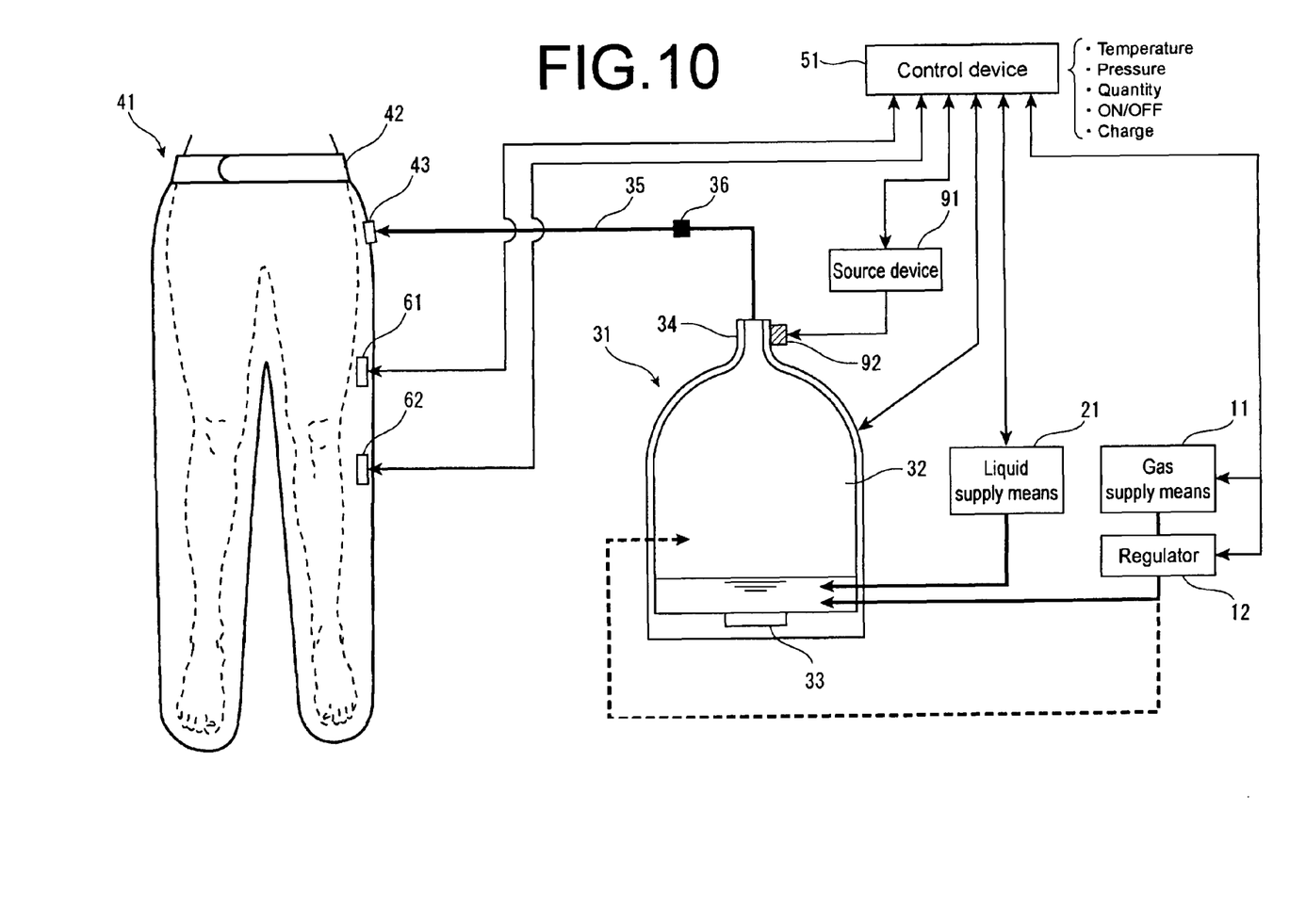
FIG. 10 A generally schematic view of the gas mist Pressure bath system depending on a third embodiment of the invention.

FIG. 10 is the whole schematic view of the gas mist pressure bath system depending on the third embodiment of this invention. This embodiment will explain the gas mist pressure bath system further having a means for charging generated mist. As to the same parts as those of the first embodiment shown in FIG. 1, the same numerals will be given, and detailed explanation will be omitted.

As shown in FIG. 10, the gas mist pressure bath system of this embodiment is arranged with an electrode 92 at the gas mist exhaust portion 34 of the gas mist supply device 31. The electrode 92 is connected to a source device 91, and the control device 51 sets voltage values and performs on-off control.

The electrode 92 supplies an electric charge (minus charge is desirable) when exhausting the mist generated by the gas mist supply device 31 from the gas mist exhaust portion 34. Thereby, the mist is made turn out charged so that adhesion to a charged material can be heightened. For example, if adhesion to the skin and the mucous membrane of the living body, an effect of increasing absorption of the gas by the mist is further heightened, and if the mist contains the above mentioned medicines, penetration into the skin and the mucous membrane can be accelerated.

For carrying out the gas mist pressure bath by using the gas mist pressure bath system of the present embodiment, the living-body pressure bath cover 41 is secured to the living body (herein, as the example, the lower extremities) and closed. The liquid is supplied from the liquid supply means 21 to the gas mist supply device 31, and then into this liquid, the gas is supplied from the gas supply means 11. Subsequently, by turning on the supersonic vibrator 33, the gas mist is generated by the supersonic wave. Then, the control device 51 controls the supplying pressure, amount, temperature and others of the liquid and the gas. The control device 51 turns on a source device 91 to give the charge to the mist. The generated gas mist is supplied from the supply portion 43 into the living-body pressure bath cover 41. When the mist is enough filled in the living-body pressure bath cover 41, the gas is directly supplied from the gas supply means 11 into the storage 32 of the gas mist supply device 31, not into the stored liquid. When the inside of the living-body pressure bath cover 41 becomes optimum pressurized and heated conditions (around 1.02 to 2.5 air pressure and around 38° C.), the control device 51 once stops supply of the gas mist or the gas in view of the measuring values of the manometer 61 and the thermometer 62, and under this condition the gas mist pressure bath is carried out.

With the structure as mentioned above, according to the gas mist pressure bath system, it is possible to control the amount, pressure and other of the gas mist within the living-body pressure bath cover by the control device, and so the gas mist pressure bath can be always carried out under the optimum condition.

Further, pressurization into the living-body pressure bath cover is easy, the gas skin-pass absorption can be more efficiently performed.

The above explanation has been made to the embodiments of the invention, but the invention is not limited to such embodiments, and so far as not deviating from the subject matter of the invention, various kinds of embodiments are, of course, available.

INDUSTRIAL APPLICABILITY

Thus, the present invention relates to the gas mist pressure bath device, in which the gas mist is prepared by pulverizing and dissolving carbon dioxide and oxygen or the mixed gas of carbon dioxide and oxygen, and the gas mist is directly contacted to the skin or mucous membrane of the living body for improving the blood circulation of the living body, and has an industrial applicability.

DESCRIPTION OF SYMBOLS

11: Gas supply means
12: Regulator
21: Liquid supply means
31: Gas mist supply device
31A, 31B: Plate
32: Storage
33: Supersonic vibrator
34: Gas mist exhaust portion
35: Gas mist supply pipe
35A: Cornice shaped pipe
36: Liquid drop removing filter
41, 41A, 41B, 41C, 41D, 41E, 41F, 81, 81A, 81B, 81C, 81D: Living-body pressure bath cover
42, 42A, 42B, 42C, 42D, 42E, 42F, 44A, 82, 82A, 82B, 82C, 82D: Stopper
43, 43A, 43B, 43C, 43D, 43E, 43F, 83, 83A, 83B, 83C, 83D: Supply portion
44F: Fastener
45F: Cover part
51: Control device
61: Manometer
62: Thermometer
71, 71A, 71B, 71C, 71D: Pressurizing part
72, 72A, 72B, 72C, 72D: Supply portion
84D: Fastener
85D: Cover part
91: Source device
92: Electrode

The invention claimed is:

1. A gas mist pressure bath system, in which a gas mist is prepared by pulverizing and dissolving carbon dioxide or oxygen or a mixed gas of carbon dioxide and oxygen, and liquid, the system comprising:
   a gas mist storage unit;
   a gas supply unit supplying carbon dioxide or oxygen or the mixed gas to the gas mist storage unit;
   a liquid supply unit supplying the liquid to the gas mist storage unit;
   a supersonic vibrator present at a bottom of the gas mist storage unit applying supersonic vibration to the liquid in the gas mist storage unit;
   a gas mist supply unit for generating and supplying the gas mist with the liquid in the gas mist storage unit while supplying carbon dioxide or oxygen or the mixed gas into the liquid in the gas mist storage unit concurrently applying the supersonic vibration to the liquid;
   a living-body cover member for covering a skin and a mucous membrane of a living body and forming a space of sealing inside the gas mist supplied from the gas mist supply unit; and
   a pressurizing unit for pressurizing an inside of the living-body cover member, the pressurizing unit being a hollow gas storage storing one of the gas mist, carbon dioxide, oxygen and the mixed gas, connecting with the living-body cover member, and being pressurized from an outside of the pressurizing unit, wherein the gas mist within the living-body cover member contacts with the skin and the mucous membrane of the living body at a predetermined pressure, the gas mist storage unit has a first plate having a plurality of pores of a predetermined pore size and a second plate having a plurality of pores of another predetermined pore size which is larger than the predetermined pore size of the first plate, for refining the gas mist above the liquid in the gas mist storage unit, and the pressurizing unit is pressurized from the outside thereof after the gas mist generated by the gas mist supply unit, carbon dioxide, oxygen or the mixed gas from the gas supply unit is supplied to an inside of the pressurizing unit.

2. A gas mist pressure bath system as set forth in claim 1, further comprising
a sensor for measuring supplying conditions of carbon dioxide or oxygen or the mixed gas, the liquid and the gas mist, and
a control unit for controlling supplies of carbon dioxide or oxygen or the mixed gas, the liquid and the gas mist based on measuring values of the sensor.

3. A gas mist pressure bath system as set forth in claim 2, wherein the control unit supplies the gas mist intermittently into the living-body cover member to perform interval pressurization on the living-body cover member.

4. A gas mist pressure bath system as set forth in claim 1, wherein the pressurizing unit pressurizes the living-body cover member intermittently to perform interval pressurization on the living-body cover member.

5. A gas mist pressure bath system as set forth in claim 1, wherein the liquid is at least one liquid selected from the group consisting of water, ionic water, physiological salt solution, ozone water, purified water, and sterilized water.

6. A gas mist pressure bath system as set forth in claim 5, wherein the liquid further contains at least one selected from the group consisting of menthol, vitamin E, vitamin C derivative, retinol, anesthetic, cyclodextrin, photocatalyst, complex of photocatalyst and apatite, hyaluronic acid, coenzyme Q10, seed oil, propolis, ethanol, gluconic acid chlorohexizine, amphoteric surface active agent, benzalkonium chloride, alkyldiamino ether glycin acetate, sodium hypochlorite, acetyl hydroperoxide, sodium sesquicarbonate, silica, povidone-iodine, sodium hydrogen carbonate, high density carbonate spring, anti-allergic agent, anti-inflammatory agent, anti-febrile agent, anti-fungus agent, anti-influenza virus agent, carcinostatic substance, anti-hyper tensive agent, cosmetic agent, and trichogen.

7. A gas mist pressure bath system as set forth in claim 5, wherein the liquid is supplied into the gas mist storage unit under a heated condition.

8. A gas mist pressure bath system as set forth in claim 1, wherein a particle size of the gas mist supplied from the gas mist supply unit to the living-body cover member is not more than 10 μm.

9. A gas mist pressure bath system as set forth in claim 2, wherein the control unit holds pressure at 1.02 to 2.5 atmospheres in the living-body cover member when taking gas mist bath.

10. A gas mist pressure bath system as set forth in claim 1, further comprising an electric charge supply unit for supplying charge to the gas mist from the gas mist supply unit.

11. A gas mist pressure bath system as set forth in claim 10, wherein the charge is minus charge.

12. A gas mist pressure bath system as set forth in claim 1, wherein the gas mist supply unit has a gas mist supply pipe for supplying the gas mist into the living-body cover member, and
the gas mist supply pipe has a filter for removing liquid drops attached to an inside of the gas mist supply pipe.

13. A gas mist pressure bath system as set forth in claim 1, wherein the gas mist supply unit has a gas mist supply pipe for supplying the gas mist into the living-body cover member, and
a whole or a part of the gas mist supply pipe is composed of a cornice shaped pipe.

14. A gas mist pressure bath system as set forth in claim 1, wherein the gas mist supply unit has a gas mist supply pipe, and
the gas mist supply pipe is provided with a check valve.

15. A gas mist pressure bath system as set forth in claim 1, wherein the living-body cover member is provided at a gas mist supply portion thereof with a check valve.

16. A gas mist pressure bath system as set forth in claim 1, wherein the gas mist storage unit has a convex forming a dome shaped top and having a curved face toward an upper portion inside thereof, and
the gas mist storage unit is formed with a gas mist exhaust portion at the dome shaped top.

17. A gas mist pressure bath system as set forth in claim 2, wherein the control unit stops the supplies of carbon dioxide or oxygen or the mixed gas from the gas supply unit when a pressure within the living-body cover member is higher than the predetermined pressure.

18. A gas mist pressure bath system as set forth in claim 1, wherein the first plate and the second plate are present at a middle of the gas mist storage unit with respect to a longitudinal direction of the gas mist storage unit.

19. A gas mist pressure bath system as set forth in claim 18, wherein the first plate is present above the second plate, and
the second plate is present on a side that the supersonic vibrator is present.

20. A gas mist pressure bath system as set forth in claim 1, wherein the hollow gas storage is connected to a supply portion of the living-body cover member so that after storing the gas mist in the gas storage, when the gas storage is pressurized, the gas mist in the gas storage is exhausted to the living-body cover member to pressurize an inside of the living-body cover member.

* * * * *